United States Patent [19]

Alving et al.

[11] Patent Number: 4,885,256

[45] Date of Patent: Dec. 5, 1989

[54] MONOCLONAL ANTIBODIES TO CHOLESTEROL AND METHODS

[75] Inventors: Carl R. Alving, Washington, D.C.; Glenn M. Swartz, Jr., Laurel, Md.

[73] Assignee: The United States of America as represented by the United States Army, Washington, D.C.

[21] Appl. No.: 875,048

[22] Filed: Jun. 17, 1986

[51] Int. Cl.⁴ .................. C07K 15/14; G01N 33/543; G01N 33/577

[52] U.S. Cl. .................. 436/518; 435/172.2; 435/240.27; 435/948; 436/548; 436/817; 436/829; 530/387; 530/809; 935/102; 935/103; 935/110

[58] Field of Search ............. 435/7, 172.2, 240, 948; 436/518, 528, 548, 817, 829; 530/387, 809; 935/110, 102, 103

[56] References Cited

U.S. PATENT DOCUMENTS 4,241,046 12/1980 Papahadjopoulos ............. 424/420
4,497,899 2/1985 Armstrong et al. ............. 436/518

OTHER PUBLICATIONS

Alving et al., in Tom et al. (Eds.) *Liposomes and Immunobiology*, Elsevier/North Holland, Inc., New York, 1980, pp. 67–78.

Baner J. I. et al., *Biochim. Biophys. Acta*, 684, 319–326, 1982.

Sato et al., *Immunochemistry*, 9, 585–587, 1972.

Sevier et al., *Clinical Chemistry*, 27, 1797–1806, 1981.

*Primary Examiner*—Robert J. Warden
*Assistant Examiner*—David A. Saunders
*Attorney, Agent, or Firm*—Werten F. W. Bellamy

[57] ABSTRACT

Monoclonal antibodies which demonstrate specific reactivity to cholesterol and methods for the detection of high levels of cholesterol by contacting biological specimens containing cholesterol with the monoclonal antibodies and measuring the formation of antigen-antibody complexes by immunosorbent assay.

11 Claims, 1 Drawing Sheet

MONOCLONAL ANTIBODIES TO CHOLESTEROL AND METHODS

The invention described herein may be manufactured, used and licensed by or for the Government for Governmental purposes without the payment to us of any royalties thereon.

FIELD OF THE INVENTION

This invention relates to monoclonal antibodies and more particularly to the use of monoclonal antibodies in methods for detection of high levels of cholesterol in biological specimens.

BACKGROUND OF THE INVENTION

Substantial work has been carried out to create satisfactory immunological assays or probes for measurement or detection of cholesterol. The most common analytical tool for such measurement is the chemical measurement of cholesterol or the use of a cholesterol-binding substance such as filipin or other polyene antibiotics. These latter substances are usually heterogeneous and difficult and expensive to produce in quantity and do not cause activation of complement as an amplifying mechanism. Accordingly, there remains a substantial need in the art for measurement of cholesterol level in biological specimens and particularly in humans.

The determination and presence of concentration of antigenic substances in biological specimens including those associated with various disorders, increasingly rely on immunoassay techniques. Commonly in the prior art such techniques are based upon formation of a complex between the antigenic substance being assayed and an antibody or antibodies in which one or the other member of the complex may be labeled as by a radioactive element which permits this detection and/or quantitative analyses after separation of the complexed labeled antigen or antibody from uncomplexed labeled antigen or antibody. In the case of a competition immunoassay technique, the antigenic substance in a sample of fluid being tested for its presence competes with a known quantity of labeled antigen for a limited quantity of antibody binding sites. Thus, the amount of labeled antigen bound to the antibody is inversely proportional to the amount of antigen in the sample. By contrast, immunometric assays employ a labeled antibody wherein the amount of labeled antibody associated with the complex is proportional to the amount of antigenic substance in the fluid sample. Such immunometric assays are found to be well suited for detection of polyvalent antigens, that is, antigenic substances which complex with two or more antibodies at the same time.

Despite the wide use of such prior art immunometric assays, problems are encountered in their use in that the antibodies are usually relatively impure and produce false positive reactions. Also, a single antibody may be used for binding the antigen for the detection or determination, which allows for error because of the problems with impure or non-specific antibodies.

In 1975, cell fusion techniques were developed to overcome the problem of lymphocyte non-viability in cell cultures. Techniques were devised for the construction of hybridoma cell lines wherein spleen lymphocytes from an animal immunized with an antigen are fused with mouse myeloma cells. The myeloma cells are immortal cells of the immune system, the term "immortal" meaning that they will continue to grow in the culture so long as they are continuously fed. The fusion of lymphocytes with myeloma cells leads to hybrid cells which have two important properties in that they have assumed the immortal life style of the myeloma cells and produce the antibody characteristic of the lymphocyte. Once the hybridoma cells are constructed, they are cloned and grown up so that groups of cells are obtained, each of which is producing only a single monoclonal antibody.

Monoclonal antibody techniques have been applied in a wide variety of areas, including immunometric assays. U.S. Pat. No. 4,486,530 to David et al, for example, discloses and claims sandwich immunometric assay techniques for determination of the presence or concentration of antigenic substances in fluids using monoclonal antibodies.

In U.S. Pat. No. 4,471,058 to Smith et al, monoclonal antibody techniques are described for the detection and/or determination of a polyvalent antigen using at least two different monoclonal antibodies. Substantial work has been done in detection and measurement of various types of antigens.

To Applicants' knowledge, however, none of this work has extended to cholesterol technology. Insofar as Applicants are aware, the only work involving the use of such technology with respect to cholesterol is the work of Banerji et al, Biochim. Biophys. Acta, 689, 319–326, (1982.) Banerji et al was concerned with membrane lipid compositions which modulate the binding specificity of a monoclonal antibody against liposomes. This work, however, was concerned with monoclonal antibodies which react with liposomes which contain low cholesterol amounts, and none of the work suggests the use of monoclonal antibodies which will react with high cholesterol liposomes. The present invention provides monoclonal antibody compositions and methods for detection and measurement of high cholesterol levels.

SUMMARY OF THE INVENTION

It is accordingly one object of the present invention to provide monoclonal antibodies which have specific reactivity to cholesterol.

A further object of the invention is to provide monoclonal antibodies which demonstrate specific reactivity to high cholesterol liposomes and provide means for detection and measurement of cholesterol levels.

A still further object of the invention is to provide novel monoclonal antibodies and methods for their preparation and use of such monoclonal antibodies in the detection of high levels of cholesterol in biological specimens.

Other objects and advantages of the present invention will become apparent as the description thereof proceeds.

In satisfaction of the foregoing objects and advantages, there is provided by this invention monoclonal antibodies which demonstrate specific reactivity to cholesterol, the antibody being characterized by its ability to induce complement-dependent damage to high-cholesterol liposomes which contain dimyristoyl phosphatidyl choline and high cholesterol, but not to low-cholesterol liposomes containing dimyristoyl phosphatidyl choline and low cholesterol. Also provided by the present invention are methods for the detection of high levels of cholesterol which comprises contacting biological specimens which contain cholesterol with the monoclonal antibodies of the invention.

The present invention also provides cholesterol antigens which may be characterized as reactive with the monoclonal antibodies of the invention. Also provided are compositions comprising a hybrid continuous cell line that produces antibodies having specific reactivity to cholesterol which comprises a cell hybrid of an animal spleen immunized with liposomes containing dimyristoyl phosphatidyl choline, cholesterol and lipid A fused to a myeloma derived from the same animal species as the spleen cell and a culture medium for the hybrid.

BRIEF DESCRIPTION OF THE DRAWINGS

Reference is now made to the drawing of the invention wherein.

DESCRIPTION OF PREFERRED EMBODIMENTS

Figure 1:
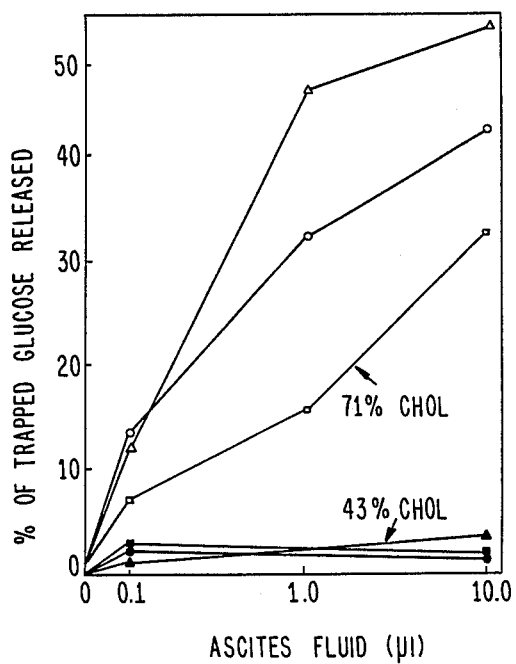
FIG. 1 shows a complement-dependent liposomal glucose release assay demonstrating reactivity of the monoclonal antibody.

As pointed out, the present invention is concerned with novel monoclonal antibodies to cholesterol. The monoclonal antibodies of the present invention have been found to demonstrate specific reactivity to cholesterol when the cholesterol is contained at high levels in biological specimens. Thus the present invention provides novel monoclonal antibodies which demonstrate specific reactivity to cholesterol, and use of those monoclonal antibodies for the detection of high levels of cholesterol in biological specimens. The present invention also provides cholesterol antigens which are reactive with the monoclonal antibodies of the invention as well as the hybridoma cell lines.

The monoclonal antibodies of the present invention may be used as probes or analytical tools for detecting high concentrations of cholesterol in biological specimens such as in lipid bilayers (liposomes) which mimic the characteristics of plasma membranes. The antibodies have exquisite specificity, which differentiates them from previous monoclonal antibodies which are obtained in a similar manner, as described in the publication by Banerji et al, Biochim. Biophys. Acta, 689, 319-326 (1982). The monoclonal antibodies disclosed in this prior publication react with liposomes containing low cholesterol whereas the present antibodies of this invention react with high cholesterol liposomes but not with the low cholesterol liposomes. Thus, the monoclonal antibody compositions and methods are different in kind from this prior work.

The monoclonal antibodies of the present invention may be used for the clinical differentiation of classes or types of plasma lipoproteins by immunological methods, in probing of biological specimens such as lipoproteins or biological membranes including plasma membranes to determine the presence of, concentration of, or location of high accumulations of cholesterol. All of these analytical methods and measurements have importance in the diagnosis and treatment of disease states involving accumulation of cholesterol or disorders involving cholesterol or lipoprotein metabolism in biological specimens and particularly including mammals such as humans.

The monoclonal antibodies of the present invention are characterized by their ability to induce complement dependent immune damage to high-cholesterol liposomes containing dimyristoyl phosphatidyl choline, cholesterol, and dicetylphosphate, but not to low cholesterol liposomes containing dimyristoyl phosphatidyl choline, low levels of cholesterol, and dicetylphosphate. In general the monoclonal antibodies to cholesterol of this invention are obtained by inducing antibodies in a mouse by immunizing the mouse with liposomes consisting of dimyristoyl phosphatidyl choline (DMPC), cholesterol, and lipid A in molar ratios of preferably 2:5:0.02. The lipid A incorporated in the liposomes was the chloroform soluble fraction obtained from Shigella Flexneri. The lipid A concentration refers to molarity of lipid A phosphate.

Fusion is then carried out as described by Banerji et al, supra. The disclosure of Banerji et al, supra, is incorporated herein by reference in its entirety.

After production of the antibodies, they are fused using cell fusion techniques with mouse myeloma cells. Fusion of the antibodies with the myeloma cells in the cell culture results in a composition comprising a hybrid continuous cell line which has the capability of producing antibodies having specific reactivity to cholesterol.

Thereafter, cultures are selected for cloning by testing for their ability to induce complement-dependent immune damage to high cholesterol liposomes which contain dimyristoyl phosphatidyl choline, cholesterol and dicetyl phosphate in ratios of 2:5:0.22, but not to low cholesterol liposomes containing these components in the ratio of 2:1.5:0.22. Thus, the mouse was immunized with high cholesterol liposomes containing lipid A and the monoclonal antibodies reacted with high cholesterol liposomes but not with low cholesterol liposomes. The selected cultures were then cloned on semisolid agarose. Cloning was carried out using the method described by M. K. Gentry, "Cloning of Hybridomas on Semisolid Agarose", Journal of Tissue Culture Methods, Vol. 9, p. 179–180, (1985), the disclosure of this publication being incorporated by reference herein in its entirety.

The preparation of spleen cells for hybridization, cell fusion, cloning and hybridoma cryopreservation included the use of a culture fluid which contained Dulbecco's modification of Eagles' medium, medium NCTC-109, oxalacetate, pyruvate, beef insulin hypoxanthine, thymidine, gentamycin, and 20% fetal calf serum. Hybridomas were derived from the fusion of $2 \times 10^8$ spleen cells, with $2 \times 10^7$ myeloma cells taken from cultures at a cell density of $6.5 \times 10^5$ cell per milliliter. After fusion, cells were distributed into a 96-well tissue culture plate at $4 \times 10^5$ cells per well. The hybridoma selected for cloning were identified by assaying the culture fluids for their ability to induce complement-dependent immune damage to high cholesterol liposomes consisting of DMPC/cholesterol/dicetylphosphate but lacking the ability to induce complement-dependent immune damage to low cholesterol liposomes consisting of the same components in molar ratios of 2:1.5:0.22.

The ascites fluids used were drawn from pristane-primed Balb/C mice that had been intraperitoneally injected with $10^6$ cloned hybrid cells and the ascites fluids were pooled together, heated at 56° C. for 30 minutes and dialyzed against 0.15 m NaCl. The pooled ascites fluid protein consisted of intraperitoneal proteins, IgG secreted by the myeloma cell line, and IgM anti-cholesterol antibody.

The enzyme linked immunosorbent assay employed for measuring antibodies to crystalline cholesterol was developed using techniques described by Smolarsky, Immunol. Meth. 38 85–93 (1980). Briefly, cholesterol was coated onto the bottom of plastic microtiter plates. Dilutions of ascites fluid were added and washed away and then alkaline phosphatase conjugated anti mouse IgM antibodies were added and washed away after incubation in the well. The substrate, p-nitrophenyl-phosphate, was added to the wells and the absorbance at 405 nm was determined for each well.

The capability of the monoclonal antibodies to detect high concentrations of cholesterol was based on the tendencies for glucose release on the liposomes identified above. The percent of trapped glucose released indicates the immunological activity of the hybridoma anti-liposome antibody. Thus, the ascites fluid containing the hybridoma antibody was tested against liposomes containing the lipid compositions. These procedures are fully set forth in the publication of Banerji et al, supra.

The monoclonal antibodies may be used as probes or analytical tools for detecting high concentrations of cholesterol in biological specimens such as lipid bilayers that mimic the characteristics of plasma membranes. The antibodies have been found to have excellent specificity to high cholesterol liposomes, but not to low cholesterol liposomes. Having the characteristics makes the antibodies imminently suitable for clinical differentiation of classes of plasma lipoproteins by immunological methods and probing of biological specimens such as lipoproteins and biological membranes to determine the presence, concentration and location of high accumulations of cholesterol. All of these characteristics cause the monoclonal antibodies to have importance in the diagnosis and treatment of disease states involving accumulation of cholesterol or disorder of cholesterol or lipoprotein metabolism.

The preferred monoclonal antibody-producing species of the present invention, anti-cholesterol hybridoma 2C5-6 has been placed on deposit with the American Type Culture Collection, 12301 Parklawn Drive, Rockville, Md. 20852 and granted Accession No. ATCC HB8995. The deposit will be maintained for a period of at least 30 years from the date of deposit and for a period of at least 5 years after the most recent request for a sample. The deposit will be made available to the scientific public upon request.

The following examples are presented to illustrate the invention but it is not to be considered as limited thereto. In the examples and throughout the specification, parts are by weight unless otherwise indicated.

EXAMPLE

One four month old Balb/c mouse obtained from Jackson Laboratories, Bar Harbor, Me., was injected intravenously with 40 ul of liposomes consisting of dimyristoyl phosphatidyl choline (DMPC), cholesterol (CHOL), and lipid A in molar ratios of 2:5:0.02. Three days after immunization the animal was sacrificed and the spleen was removed. Spleen cells were then hybridized with plasmacytoma cells from the myeloma cell line P3-X63. Following cell fusion cell culture supernatants were assayed for complement-dependent immune damage to liposomes containing DMPC/CHOL in ratios of 2:5. The hybridomas selected for cloning were identified further by their abilities to induce complement-dependent immune damage to DMPC/CHOL/DCP in ratios of 2:5:0.22 liposomes but not to DMPC/CHOL/DCP liposomes in the ratios of 2:1.5:0.22. Eight candidates were selected for cloning. Cloning was carried out using the method described by M. K. Gentry, J. Tissue Culture Methods, Vol. 9, p. 179–180 (1985). Clone populations were expanded and culture supernatants were tested again against both high cholesterol and low cholesterol liposomes. Three clones were chosen for production of ascites fluid. Vials containing $10^8$ cells per milliliter of each clone were injected into pristane-primed Balb/c mice. The ascites fluid obtained was tested against high cholesterol and low cholesterol liposomes.

In the accompanying FIG. 1, there is shown a graph which shows the complement-dependent antibody-mediated glucose release from high cholesterol liposomes but not from low-cholesterol liposomes. The graph shows this measurement with respect to the percent of trapped glucose released by the ascites fluid. Each curve in the graph represents murine ascites fluid containing a separate antibody from a different clone. The results of the graph indicate substantial percentages of glucose released in the high-cholesterol liposomes, but not from low cholesterol liposomes.

Figure 2:
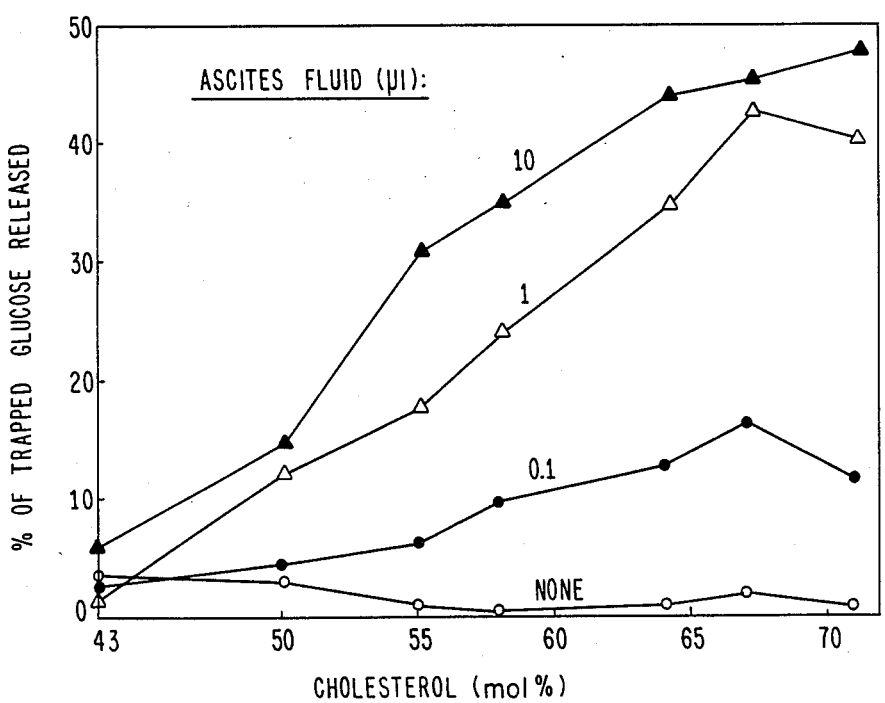
FIG. 2 shows that the event of complement-dependent immune damage to liposomes is dependent both on the amount of antibody employed and the cholesterol concentration in the liposomes.

FIG. 2 is a dose response curve showing cholesterol dependence for complement-dependent immune damage to liposomes, again with respect to the percent of trapped glucose released. Each curve in FIG. 2 represents a different concentration of ascites fluid containing one of the anti-cholesterol antibodies. Thus, FIG. 2 shows that the vent of complement-dependent immune damage to liposomes is dependent both on the amount of antibody employed and the cholesterol concentration in the liposomes.

The following Table shows a solid phase enzyme linked immunosorbent assay (ELISA) which demonstrates that the antibodies can bind to crystalline cholesterol. In this table the reactivity of the anti-cholesterol monoclonal antibody is shown with respect to the ascites fluid in the concentrations shown. The solutions used and the antigen are also indicated.

TABLE

Reactivity of Anti-Cholesterol Monoclonal Antibody

| Solution for Blocking, Diluting and Washing | Antigen (μg/Well) | $A_{405} \times 10^3$ Corrected for Blank Anti-Cholesterol (C) Ascites Fluid | | |
|---|---|---|---|---|
| | | $10^{-2}$ | $10^{-3}$ | $10^{-4}$ |
| PBS - 0.3% Gelatin 1 mM EDTA | None | 52 | 15 | 13 |
| | CHOL 50 | 1644 | 157 | 68 |
| | CHOL 12.5 | 1399 | 416 | 145 |
| | CHOL 2.5 | 1838 | 271 | 62 |
| | CHOL 0.5 | 1408 | 74 | 66 |
| | CHOL 0.1 | 1802 | 101 | 58 |
| | CHOL 0.02 | 565 | 235 | 58 |
| PBS - 1% BSA | None | 330 | 158 | 115 |
| | CHOL 50 | 1772 | 1833 | 766 |
| | CHOL 12.5 | 1225 | 1106 | 383 |
| | CHOL 2.5 | 995 | 920 | 286 |
| | CHOL 0.5 | 1472 | 968 | 311 |
| | CHOL 0.1 | 1457 | 927 | 333 |
| | CHOL 0.02 | 1012 | 482 | 210 |

As indicated, this Table demonstrates that the antibodies can in fact bind to crystalline cholesterol and demonstrates the exquisite specificity of the monoclonal antibodies of the invention.

The invention has been described herein with reference to certain preferred embodiments. However, as obvious variations thereon will become apparent to those skilled in the art, the invention is not to be considered as limited thereto.

What is claimed is:

1. A monoclonal antibody demonstrating reactivity to cholesterol in biological specimens, the antibody being characterized by its ability to induce complement-dependent immune damage to high-cholesterol liposomes containing dimyristoyl phosphatidyl choline, cholesterol and dicetyl phosphate, but not low-cholesterol liposomes containing dimyristoyl phosphatidyl choline, cholesterol and dicetyl phosphate.

2. A monoclonal antibody according to claim 1 which has the characteristics of the antibody produced by ATCC HB 8995.

3. The monoclonal antibody according to claim 1 wherein the high-cholesterol liposomes contain dimyristoyl phosphatidyl choline, cholesterol and dicetyl phosphate in molar ratios of 2:5:0.22.

4. A composition comprising a hybrid continuous cell line that produces antibody having reactivity to cholesterol wherein said cell line comprises a hybrid of (1) a spleen cell from an animal immunized with liposomes containing dimyristoyl phosphatidyl choline, cholesterol and dicetyl phosphate fused to (2) a myeloma cell derived from the same animal species as the spleen cell.

5. A composition according to claim 4 wherein the animal spleen cell is a mouse spleen cell.

6. A composition according to claim 5 wherein the animal is immunized with liposomes containing dimyristoyl phosphatidyl choline, cholesterol and lipid-A in molar ratios of 2:5:0.02.

7. A method for the detection of cholesterol in biological specimens which comprises the steps of (1) contacting the biological specimens which may contain cholesterol with antibodies which demonstrate reactivity to cholesterol as evidenced by the ability to induce complement-dependent immune damage to high-cholesterol liposomes containing dimyristoyl phosphatidyl choline, cholesterol and dicetyl phosphate, but not to low-cholesterol liposomes containing dimyristoyl phosphatidyl choline, cholesterol and dicetyl phosphate, (2) measuring the formation of antigen-antibody complexes by immunosorbent assays and (3) relating the measurements of step (2) to the presence of or concentration of cholesterol in biological specimens.

8. A method according to claim 7 wherein the biological specimens comprise lipid bilayers which mimic the characteristics of lipid bilayers of plasma membranes.

9. A method according to claim 7 wherein the antibodies have the identifying characteristics of an antibody produced by ATCC HB 8995.

10. A method according to claim 7 wherein the measurement of the formation of the antigen antibody complexes is carried out by solid phase enzyme-linked immunosorbent assays.

11. A method according to claim 7 wherein the biological specimen is from a mammal.

* * * * *